US 7,744,655 B2

(12) United States Patent
De Boni et al.

(10) Patent No.: US 7,744,655 B2
(45) Date of Patent: Jun. 29, 2010

(54) PROCESS FOR DYEING THE HAIR USING AN ANIONIC COLOURED POLYMER

(75) Inventors: Maxime De Boni, Paris (FR); Bruno Laguitton, Kremlin Bicetre (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/795,383

(22) PCT Filed: Mar. 14, 2006

(86) PCT No.: PCT/EP2006/003301

§ 371 (c)(1),
(2), (4) Date: Mar. 11, 2008

(87) PCT Pub. No.: WO2006/097360

PCT Pub. Date: Sep. 21, 2006

(65) Prior Publication Data

US 2008/0282481 A1    Nov. 20, 2008

Related U.S. Application Data

(60) Provisional application No. 60/678,206, filed on May 6, 2005.

(30) Foreign Application Priority Data

Mar. 14, 2005   (FR)   .................................. 05 50648

(51) Int. Cl.
*A61Q 5/10*   (2006.01)

(52) U.S. Cl. ......................... 8/405; 8/435; 8/552; 8/554
(58) Field of Classification Search ..................... 8/405, 8/435, 455, 552, 554
See application file for complete search history.

(56) References Cited

U.S. PATENT DOCUMENTS

| 4,911,731 | A  | * | 3/1990  | Loveless et al. ................. 8/405 |
| 4,943,430 | A  |   | 7/1990  | Hefford et al. |
| 6,602,303 | B2 | * | 8/2003  | Laurent et al. .................. 8/406 |
| 2004/0253196 | A1 | * | 12/2004 | Soane et al. ............. 424/70.11 |

OTHER PUBLICATIONS

STIC Search Report dated Feb. 27, 2009.*
International Search Report for PCT/EP2006/003301, dated Jun. 30, 2006.
Search Report for FR 0550648, dated Jan. 25, 2006.

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

The present invention relates to a process for dyeing keratin fibres, which comprises the application to the fibres of a composition containing at least one cationic polymer, rinsing of the keratin fibres, the application of a composition containing at least one anionic colored polymer, and rinsing of the keratin fibres.

Such a process makes it possible to obtain an improvement in the coloration of the keratin fibres.

17 Claims, No Drawings

PROCESS FOR DYEING THE HAIR USING AN ANIONIC COLOURED POLYMER

CROSS-REFERENCE TO RELATED APPLICATIONS

This application is a national phase application of International Application No. PCT/EP2006/003301, filed Mar. 14, 2006, and claims the priority of French Application No. 0550648, filed Mar. 14, 2005, and the benefit of U.S. Provisional Application No. 60/678,206, filed May 6, 2005, the content of all of which is incorporated herein by reference.

The invention relates to a process for dyeing the hair using an anionic coloured polymer. The invention also relates to a dyeing kit containing, firstly, a composition containing the anionic coloured polymer, and, secondly, a composition containing a cationic polymer.

It is known practice to dye keratin fibres, and in particular human hair, with dye compositions that allow temporary colorations to be obtained. Temporary colorations are colorations that are predominantly removed on the first shampoo wash, while at the same time maintaining a certain level of resistance to water or rubbing. For example, patent applications EP 747 036 and EP 852 843 propose temporary colorations using water-dispersible coloured polymers containing sulfo groups, which comprise carbonyloxy bonds and a chromophore. U.S. Pat. No. 4,911,731 describes a temporary dyeing process that consists in applying to the hair a complex formed from a particular cationic polymer and an anionic coloured polymer.

However, these colorations do not have high dyeing power. For this reason, they do not generally constitute a true coloration, but make it possible to correct fading of a permanent or semi-permanent coloration. Furthermore, these colorations are generally poorly visible on dark hair. Lastly, these colorations are not followed by rinsing, which poses large staining problems.

The aim of the present invention is to provide a novel process for the temporary dyeing of keratin fibres that does not have the drawbacks of the colorations of the prior art, in particular strong colorations that are visible on both fair hair and dark hair, which are resistant to water or to rubbing, but which are also predominantly removed on the first shampoo wash.

This aim is achieved with the present invention, one subject of which is a process for dyeing keratin fibres, comprising:

the application to the fibres of a composition containing at least one cationic polymer, rinsing of the keratin fibres, the application of a composition containing at least one anionic coloured polymer, and rinsing of the keratin fibres.

The process of the present invention makes it possible in particular to obtain a temporary coloration of keratin fibres that does not present any staining problems and that makes it possible to visibly colour bleached or natural fair hair and also natural dark hair or dark hair that has been dyed, for example by direct or oxidation dyeing.

For the purposes of the present invention, the expression "cationic polymer" denotes any polymer containing cationic groups and/or groups that can be ionized into cationic groups. Examples that may be mentioned include ammoniums and quaternary ammoniums.

According to the invention, the compositions containing the cationic polymer or the anionic coloured polymer are preferably aqueous compositions. The compositions according to the invention may be in solution or emulsion form.

Advantageously, the cationic polymers that may be used in accordance with the present invention may be chosen from those described especially in EP 337 354, FR 2 270 846, FR 2 383 660, FR 2 598 611, FR 2 470 596 and FR 2 519 863.

The preferred cationic polymers are chosen from those containing units comprising primary, secondary, tertiary and/or quaternary amine groups, which either may form part of the main polymer chain or may be borne by a side substituent directly attached thereto.

The cationic polymers used generally have a number-average molecular mass of between 500 and $5 \times 10^6$ approximately and preferably between $10^3$ and $3 \times 10^6$ g/mol.

Among the cationic polymers that may be mentioned more particularly are polymers of the polyamine, polyamino amide and polyquaternary ammonium type.

These are known products and are described in particular in patents FR 2 505 348 and FR 2 542 997. Among the said polymers, mention may be made of the following polymers.

(1) Homopolymers or copolymers derived from acrylic or methacrylic esters or amides and comprising at least one of the units of formula (I), (II), (III) or (IV) below:

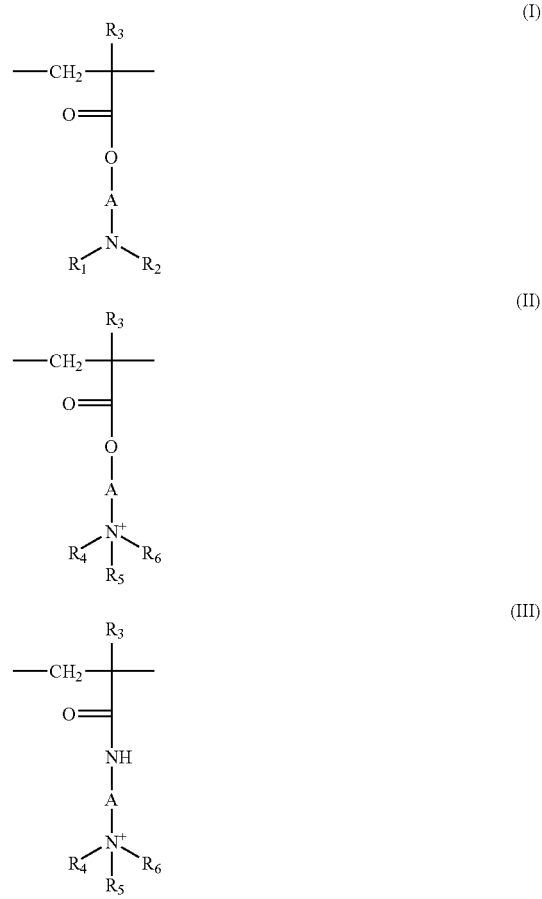

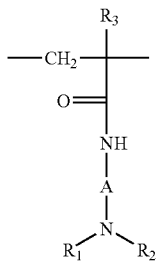 (IV)

in which:

R$_3$, which may be identical or different, denote a hydrogen atom or a CH$_3$ radical;

A, which may be identical or different, represent a linear or branched C$_1$-C$_6$ and preferably C$_2$-C$_3$ alkyl group or a C$_1$-C$_4$ hydroxyalkyl group;

R$_4$, R$_5$ and R$_6$, which may be identical or different, represent a C$_1$-C$_{18}$ alkyl group or a benzyl radical, and preferably a C$_1$-C$_6$ alkyl group;

R$_1$ and R$_2$, which may be identical or different, represent hydrogen or a C$_1$-C$_6$ alkyl group, and preferably methyl or ethyl;

X denotes an anion derived from a mineral or organic acid, such as a methosulfate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower (C$_1$-C$_4$) alkyls, acrylic or methacrylic acids or esters thereof, vinyllactams such as vinylpyrrolidone or vinyl-caprolactam, and vinyl esters.

Thus, among these polymers of family (1), mention may be made of:

copolymers of acrylamide and of dimethylaminoethyl methacrylate quaternized with dimethyl sulfate or with a dimethyl halide, such as the product sold under the name Hercofloc by the company Hercules, the copolymers of acrylamide and of methacryloyloxyethyltrimethylammonium chloride described, for example, in EP 80 976 and sold under the name Bina Quat P 100 by the company Ciba Geigy, the copolymer of acrylamide and of methacryloyloxy-ethyltrimethylammonium methosulfate sold under the name Reten by the company Hercules, quaternized or non-quaternized vinylpyrrolidone/dialkylaminoalkyl acrylate or methacrylate copolymers, such as the products sold under the name "Gafquat" by the company ISP, for instance "Gafquat 734" or "Gafquat 755", or alternatively the products known as "Copolymer 845, 958 and 937". These polymers are described in FR 2 077 143 and FR 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, and quaternized vinylpyrrolidone/dimethylaminopropyl methacrylamide copolymers such as the product sold under the name "Gafquat HS100" by the company ISP.

(2) The cellulose ether derivatives comprising quaternary ammonium groups, which are described in FR 1 492 597, and in particular the polymers sold under the names "JR" (JR 400, JR 125, JR 30M) or "LR" (LR 400, LR 30M) by the company Union Carbide Corporation. These polymers are also defined in the CTFA dictionary as hydroxyethylcellulose quaternary ammoniums that have reacted with an epoxide substituted with a trimethylammonium group.

(3) Cationic cellulose derivatives such as the copolymers of cellulose or cellulose derivatives grafted with a water-soluble quaternary ammonium monomer, described especially in U.S. Pat. No. 4,131,576, such as hydroxyalkylcelluloses, for instance hydroxymethyl-, hydroxyethyl- or hydroxypropylcelluloses grafted especially with a methacryloylethyltrimethylammonium, methacrylamidopropyltrimethylammonium or dimethyldiallylammonium salt.

The commercial products corresponding to this definition are more particularly the products sold under the name "Celquat L 200" and "Celquat H 100" by the company National Starch.

(4) The cationic guar gums described more particularly in U.S. Pat. No. 3,589,578 and U.S. Pat. No. 4,031,307, such as those containing trialkylammonium cationic groups. Use is made, for example, of guar gums modified with a salt (e.g. chloride) of 2,3-epoxypropyltrimethylammonium.

Such products are sold especially under the trade names Jaguar C13S, Jaguar C15, Jaguar C17 and Jaguar C162 by the company Meyhall.

(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, and also the oxidation and/or quaternization products of these polymers. Such polymers are described, in particular, in FR 2 162 025 and FR 2 280 361.

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in FR 2 252 840 and FR 2 368 508.

Polyamino amide derivatives resulting from the condensation of polyalkylene polyamines with polycarboxylic acids followed by alkylation with difunctional agents. Mention may be made, for example, of adipic acid/dialkylaminohydroxyalkyldialkylene-triamine polymers in which the alkyl radical is C$_1$-C$_4$ and preferably denotes methyl, ethyl or propyl. Such polymers are described in particular in FR 1 583 363.

Among these derivatives, mention may be made more particularly of the adipic acid/dimethylamino-hydroxypropyl/diethylenetriamine polymers sold under the name "Cartaretine F, F4 or F8" by the company Sandoz.

(7) The polymers obtained by reaction of a polyalkylene polyamine containing two primary amine groups and at least one secondary amine group with a dicarboxylic acid chosen from diglycolic acid and saturated $C_3$-$C_8$ aliphatic dicarboxylic acids. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. No. 3,227,615 and U.S. Pat. No. 2,961,347.

Polymers of this type are sold in particular under the name "Hercosett 57", "PD 1700" or "Delsette 101" by the company Hercules.

(8) Cyclopolymers of alkyldiallylamine or of dialkyldiallylammonium, such as the homopolymers or copolymers containing, as main constituent of the chain, units corresponding to formula (V) or (VI):

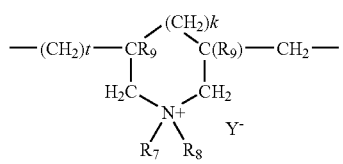

(V)

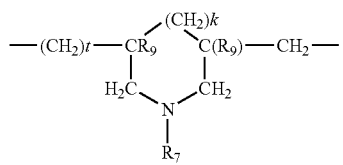

(VI)

in which formulae k and t are equal to 0 or 1, the sum k+t being equal to 1; $R_9$ denotes a hydrogen atom or a methyl radical; $R_7$ and $R_8$, independently of each other, denote a $C_1$-$C_8$ alkyl group, a hydroxyalkyl group in which the alkyl group is $C_1$-$C_5$, an amidoalkyl group in which the alkyl is $C_1$-$C_4$; $R_7$ and $R_8$ can also denote, together with the nitrogen atom to which they are attached, a heterocyclic group such as piperidyl or morpholinyl; $R_7$ and $R_8$, independently of each other, preferably denote a $C_1$-$C_4$ alkyl group; $Y^-$ is an organic or mineral anion such as bromide, chloride, acetate, borate, citrate, tartrate, bisulfate, bisulfite, sulfate or phosphate. These polymers are described in particular in FR 2 080 759 and FR 2 190 406.

Among the polymers defined above, mention may be made more particularly of the dimethyldiallyl-ammonium chloride homopolymer sold under the name "Merquat 100" by the company Nalco (and its homologues of low weight-average molecular mass) and the copolymers of diallyldimethylammonium chloride and of acrylamide, sold under the name "Merquat 550".

(9) The quaternary diammonium polymer containing repeating units corresponding to the formula:

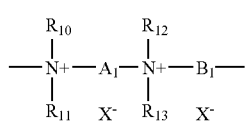

(VII)

in which formula:

$R_{10}$, $R_{11}$, $R_{12}$ and $R_{13}$, which may be identical or different, represent $C_1$-$C_{20}$ aliphatic, alicyclic or arylaliphatic radicals or hydroxyalkylaliphatic radicals in which the alkyl radical is $C_1$-$C_4$, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

$A_1$ and $B_1$ represent $C_2$-$C_{20}$ polymethylene groups which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO-D-OC—$(CH_2)_n$— in which n is between 1 and 100 and preferably between 1 and 50, and D denotes:

a) a glycol residue of formula: —O—Z—O—, where Z denotes a linear or branched hydrocarbon-based radical or a group corresponding to one of the following formulae: —($CH_2$—$CH_2$—O)$_x$—$CH_2$—$CH_2$—; —[$CH_2$—CH($CH_3$)—O]$_y$—$CH_2$—CH($CH_3$)—, where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or alternatively the radical —$CH_2$—$CH_2$—S—S—$CH_2$—$CH_2$—;

d) a ureylene group of formula: —NH—CO—NH—.

Preferably, $X^-$ is an anion such as chloride or bromide.

These polymers generally have a number-average molecular mass of between 1000 and 100 000 g/mol.

Polymers of this type are described in particular in FR 2 320 330, FR 2 270 846, FR 2 316 271, FR 2 336 434, FR 2 413 907, U.S. Pat. No. 2,273,780, U.S. Pat. No. 2,375,853, U.S. Pat. No. 2,388,614, U.S. Pat. No. 2,454,547, U.S. Pat. No. 3,206,462, U.S. Pat. No. 2,261,002, U.S. Pat. No. 2,271,378, U.S. Pat. No. 3,874,870, U.S. Pat. No. 4,001,432, U.S. Pat. No. 3,929,990, U.S. Pat. No. 3,966,904, U.S. Pat. No. 4,005,193, U.S. Pat. No. 4,025,617, U.S. Pat. No. 4,025,627, U.S. Pat. No. 4,025,653, U.S. Pat. No. 4,026,945 and U.S. Pat. No. 4,027,020.

It is more particularly possible to use polymers that consist of repeating units corresponding to the following formula (VIII):

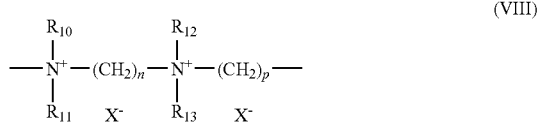

in which $R_{10}$, $R_{11}$, $R_{12}$ and $R_{13}$, which may be identical or different, denote a $C_1$-$C_4$ alkyl or hydroxyalkyl radical, n and p are integers ranging from 2 to 20 approximately, and $X^-$ is an anion derived from a mineral or organic acid.

(10) Polyquaternary ammonium polymers consisting of repeating units of formula (IX):

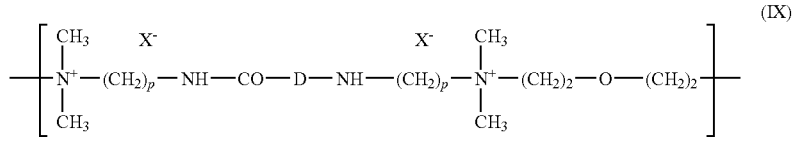

in which p denotes an integer ranging from 1 to 6 approximately, D may be zero or may represent a group $-(CH_2)_r-CO-$ in which r denotes a number equal to 4 or 7, and $X^-$ is an anion.

Such polymers may be prepared according to the processes described in U.S. Pat. No. 4,157,388, U.S. Pat. No. 4,702,906 and U.S. Pat. No. 4,719,282. They are especially described in patent application EP 122 324.

Among these polymers, examples that may be mentioned include the products "Mirapol A 15", "Mirapol AD1", "Mirapol AZ1" and "Mirapol 175" sold by the company Miranol.

(11) Quaternary polymers of vinylpyrrolidone and of vinylimidazole, for instance the products sold under the names Luviquat FC 905, FC 550 and FC 370 by the company BASF.

(12) Polyamines such as Polyquart H sold by Cognis, which is given under the reference name "Polyethylene glycol (15) tallow polyamine" in the CTFA dictionary.

(13) Crosslinked methacryloyloxy($C_1$-$C_4$)alkyltri($C_1$-$C_4$)-alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethyl-ammonium chloride copolymer (20/80 by weight) in the form of a dispersion containing 50% by weight of the said copolymer in mineral oil can be used more particularly. This dispersion is sold under the name "Salcare® SC 92" by the company Ciba. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Ciba.

Other cationic polymers which can be used in the context of the invention are polyalkyleneimines, in particular polyethyleneimines, especially polylysines or polyarginines; polymers containing vinylpyridine or vinylpyridinium units; condensates of polyamines and of epichlorohydrin; quaternary polyureylenes and chitin derivatives.

Among all the cationic polymers which may be used in the context of the present invention, it is preferred to use the polymers of families (1), (8), (9), (10) and (13) and even more preferentially the polymers containing repeating units of formulae (W) and (U) below:

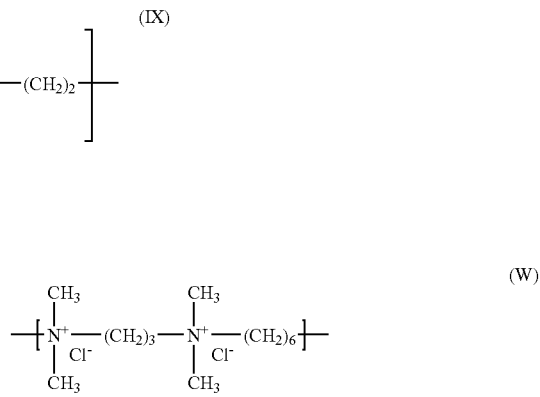

and especially those whose molecular weight, determined by gel permeation chromatography, is between 9500 and 9900;

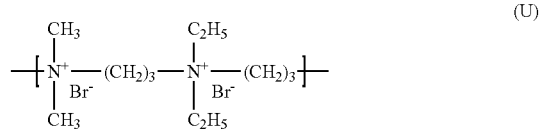

and in particular those whose molecular weight, determined by gel permeation chromatography, is about 1200.

The amount of cationic polymer in the composition that is useful for the invention may range from 0.01% to 20% by weight relative to the total weight of the composition, and preferably from 0.1% to 10% by weight relative to the total weight of the composition. This composition is preferably an aqueous composition.

The process of the invention also uses an anionic coloured polymer. The term "anionic coloured polymer" means any polymer skeleton comprising a chromophore either in the skeleton or as a pendent group, on condition that the polymer skeleton and/or the chromophore bears at least one negative charge. According to one preferred embodiment, the coloured polymer comprises one or more chromophores as pendent group.

Such a polymer comprises at least one unit represented by:

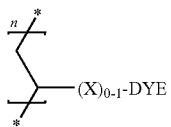

in which DYE represents the chromophore that is attached to the polymer skeleton either directly or via a saturated or unsaturated, linear or branched hydrocarbon-based chain containing from 1 to 10 carbon atoms and preferably from 1 to 6 carbon atoms, at least one of the carbon atoms of which may be replaced with a heteroatom chosen from sulfur, silicon, phosphorus, selenium, nitrogen and oxygen or an $SO_2$ group, the hydrocarbon-based chain possibly being substituted or unsubstituted, the polymer comprising at least one negative charge that may be borne either by the chromophore or by the polymer skeleton, and n represents the number of repeating units of this type present in the polymer. Generally, n is between 1 and 1000 and preferably between 1 and 500. These polymers may be block polymers or random polymers.

Substituents on the carbon-based chain that may be mentioned include alkyl, hydroxyl, alkoxy and hydroxyalkyl radicals, halogens, amino radicals or amino radicals mono- or disubstituted with an alkyl or hydroxyalkyl radical.

Chromophores that may be mentioned include the radicals derived from nitrobenzene, azo, phenothiazine, xanthene, phenanthridine, phthalocyanin and triarylmethane-based dyes, and those obtained from direct dyes containing a carbonyl group. Among the chromophores of this type, examples that may be mentioned include chromophores derived from dyes chosen from acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes.

According to one preferred embodiment, the chromophore is an anionic chromophore. In particular, the chromophore may be substituted with at least one sulfonate, carboxylate, phosphate, phosphonate or sulfate group. Examples that may be mentioned include the radicals derived from acidic nitro direct dyes, acidic azo dyes, acidic azine dyes, acidic triarylmethane dyes, acidic indoamine dyes and non-quinone acidic natural dyes.

Anionic coloured polymers that may be mentioned include those described in U.S. Pat. No. 4,911,731, U.S. Pat. No. 6,306,182, EP 852 943, EP 747 036, U.S. Pat. No. 4,381,260, U.S. Pat. No. 4,314,808, U.S. Pat. No. 4,144,252 and U.S. Pat. No. 4,051,138.

According to one variant, the anionic coloured polymer corresponds to the formula:

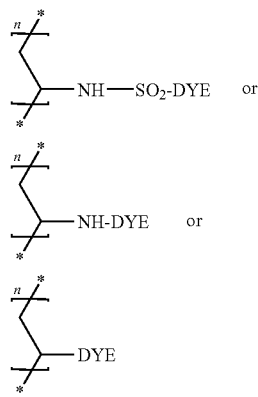

in which DYE is an anionic chromophoric radical.

By way of example, mention may be made of the following anionic coloured polymers:

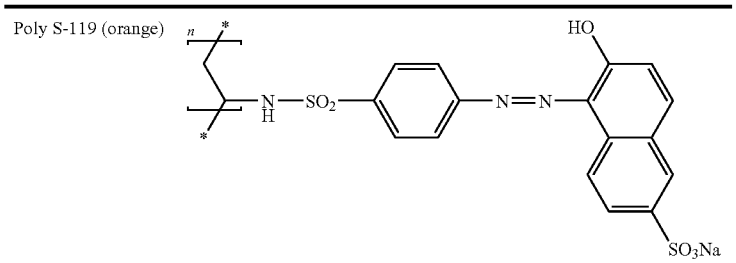

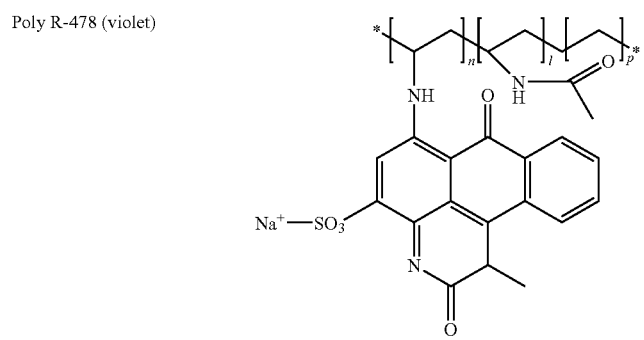

PAZO (yellow)

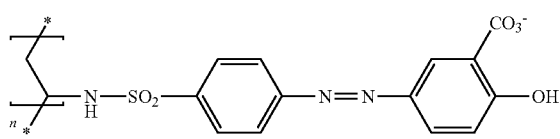

The amount of anionic coloured polymer in the composition applied to the fibres is generally between 0.01% and 20% and preferably between 0.1% and 5%. According to one particular embodiment, the composition is an aqueous composition.

According to one variant, one of the compositions applied to the keratin fibres contains an organic and/or mineral salt. An organic salt that may be mentioned is sodium citrate. Mineral salts that may be mentioned include sodium chloride, ammonium sulfate, magnesium chloride and calcium chloride. The salt is preferably contained in the solution containing the cationic polymer.

The amount of organic or mineral salts is generally between $10^{-4}$ and 2 mol/l and preferably between $10^{-3}$ and 1 mol/l. According to one particularly preferred embodiment, the amount of salts is between $10^{-2}$ and 1 mol/l.

According to one particular embodiment, the composition containing the anionic coloured polymer may also comprise one or more organic or mineral salts as defined above.

The compositions containing either the cationic polymer or the anionic coloured polymer generally consist of water or of a mixture of water and of at least one organic solvent to dissolve the compounds that are not sufficiently water-soluble. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether and diethylene glycol monomethyl ether and monoethyl ether, and also aromatic alcohols, for instance benzyl alcohol and phenoxyethanol, and mixtures thereof.

The solvents are preferably present in proportions preferably between 1% and 40% by weight approximately and even more preferentially between 5% and 30% by weight approximately relative to the total weight of the composition.

The compositions that are useful in the process of the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

According to one particular embodiment, the compositions applied to the keratin fibres do not contain any additives bearing charges opposite that of the polymer present in the composition.

In particular, the compositions that are useful may contain as conditioning agent linear, cyclic, branched or non-branched, volatile or non-volatile silicones. These silicones may be in the form of oils, resins or gums, and may in particular be polyorganosiloxanes that are insoluble in the cosmetically acceptable medium.

The organopolysiloxanes are defined in greater detail in Walter Noll's "Chemistry and Technology of Silicones" (1968) Academic Press. They can be volatile or non-volatile.

When they are volatile, the silicones are more particularly chosen from those having a boiling point of between 60° C. and 260° C., and even more particularly from:

(i) cyclic silicones containing from 3 to 7 and preferably 4 to 5 silicon atoms. These are, for example, octamethylcyclotetrasiloxane sold in particular under the name "Volatile Silicone 7207" by Union Carbide or "Silbione 70045 V 2" by Rhodia, decamethylcyclopentasiloxane sold under the name "Volatile Silicone 7158" by Union Carbide, and "Silbione 70045 V 5" by Rhodia, and mixtures thereof.

Mention may also be made of cyclocopolymers of the dimethylsiloxane/methylalkylsiloxane type, such as "Volatile Silicone FZ 3109" sold by the company Union Carbide, having the chemical structure:

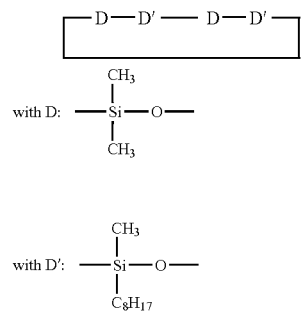

Mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones containing 2 to 9 silicon atoms and having a viscosity of less than or equal to $5 \times 10^{-6}$ m$^2$/s at 25° C. An example is decamethyltetrasiloxane sold in particular under the name "SH 200" by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

Among the non-volatile silicones that may be mentioned especially are polyalkylsiloxanes, polyarylsiloxanes, polyalkylarylsiloxanes, silicone gums and resins, and polyorganosiloxanes modified with organofunctional groups, and mixtures thereof.

The organomodified silicones that may be used in accordance with the invention are silicones as defined above and containing in their structure one or more organofunctional groups attached via a hydrocarbon-based group.

Among the organomodified silicones that may be mentioned are polyorganosiloxanes containing:

- polyethyleneoxy and/or polypropyleneoxy groups optionally containing $C_6$-$C_{24}$ alkyl groups, such as the products known as dimethicone copolyol sold by the company Dow Corning under the name DC 1248 or the oils Silwet® L 722, L 7500, L 77 and L 711 from the company Union Carbide and the ($C_{12}$)alkylmethicone copolyol sold by the company Dow Corning under the name Q2 5200;
- substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$-$C_4$ aminoalkyl groups;
- thiol groups such as the products sold under the names "GP 72 A" and "GP 71" from Genesee;
- alkoxylated groups such as the product sold under the name "Silicone Copolymer F-755" by SWS Silicones and Abil Wax® 2428, 2434 and 2440 by the company Goldschmidt;
- hydroxylated groups such as the polyorganosiloxanes containing a hydroxyalkyl function, described in French patent application FR-A-85 16334;
- acyloxyalkyl groups such as, for example, the polyorganosiloxanes described in U.S. Pat. No. 4,957,732;
- anionic groups of the carboxylic acid type, such as, for example, in the products described in patent EP 186 507 from the company Chisso Corporation, or of alkylcarboxylic type, such as those present in the product X-22-3701E from the company Shin-Etsu; 2-hydroxyalkyl sulfonate; 2-hydroxyalkyl thiosulfate such as the products sold by the company Goldschmidt under the names "Abil® S201" and "Abil® S255";
- hydroxyacylamino groups, such as the polyorganosiloxanes described in patent application EP 342 834. Mention may be made, for example, of the product Q2-8413 from the company Dow Corning.

The silicone oils that may be used in the compositions according to the invention are volatile or non-volatile polymethylsiloxanes containing a linear or cyclic silicone chain, which are liquid or pasty at room temperature, especially cyclopolydimethylsiloxanes (cyclomethicones) such as cyclohexasiloxane; polydimethylsiloxanes comprising alkyl, alkoxy or phenyl groups, which are pendent or at the end of a silicone chain, these groups containing from 2 to 24 carbon atoms; phenylsilicones, for instance phenyltrimethicones, phenyldimethicones, phenyltrimethylsiloxydiphenylsiloxanes, diphenyl-dimethicones, diphenylmethyldiphenyltrisiloxanes, 2-phenylethyltrimethyl siloxysilicates, polymethylphenylsiloxanes; and mixtures thereof.

The silicone gums that may be used in the compositions according to the invention are polydiorganosiloxanes with a high molecular mass, of between 200 000 and 2 000 000, used alone or as a mixture in a solvent chosen from volatile silicones, polydimethylsiloxane oils, polyphenylmethylsiloxane oils, polydiphenyldimethylsiloxane oils, isoparaffins, methylene chloride, pentane and hydrocarbons, or mixtures thereof.

A silicone gum with a molecular weight of less than 1 500 000 is preferably used. The silicone gums are, for example, polydimethylsiloxanes, polyphenylmethylsiloxanes, poly (diphenylsiloxane-dimethylsiloxanes), poly(dimethylsiloxanemethylvinyl-siloxanes), poly(dimethylsiloxanephenylmethylsiloxanes) or poly(diphenylsiloxanedimethylsiloxanemethylvinylsiloxanes).

These silicone gums may be terminated at a chain end with trimethylsilyl or dimethylhydroxysilyl groups.

The silicone resins that may be used in the compositions according to the invention are crosslinked siloxane systems containing units $R_2SiO_{2/2}$, $RSiO_{3/2}$ or $SiO_{4/2}$, in which R represents a hydrocarbon-based group containing from 1 to 6 carbon atoms or a phenyl group. Among these products, the ones that are particularly preferred are those in which R denotes a lower ($C_1$-$C_6$) alkyl radical or a phenyl radical.

As conditioning agents, chitosans may also be used. The chitosans and chitosan derivatives that may be used are in particular chitosan salts such as chitosan acetate, lactate, glutamate, gluconate or pyrrolidonecarboxylate.

Among these compounds, mention may be made of chitosan having a degree of deacetylation of 90.5% by weight, sold under the name Kytan Brut Standard by the company Aber Technologies, and chitosan pyrrolidonecarboxylate sold under the name Kytamer® PC by the company Amerchol.

The concentration of conditioning agent(s) in the composition(s) according to the present invention may range from 0.01% to 10%, preferably from 0.05% to 5% and even more preferentially from 0.1% to 3% by weight relative to the total weight of the composition.

The compositions that are useful in the process of the invention may also contain at least one thickening polymer, also known as "rheology modifiers".

The thickeners may be chosen from fatty acid amides (coconut diethanolamide or monoethanolamide, or oxyethylenated monoethanolamide of carboxylic acid alkyl ether), cellulose-based thickeners (hydroxyethylcellulose, hydroxypropylcellulose or carboxymethylcellulose), guar gum and its derivatives (hydroxypropylguar), gums of microbial origin (xanthan gum, scleroglucan gum), crosslinked homopolymers of acrylic acid or of acrylamidopropanesulfonic acid, and associative polymers as described below.

The associative polymers that may be used according to the invention are water-soluble polymers capable, in an aqueous medium, of reversibly combining with each other or with other molecules.

Their chemical structure comprises hydrophilic zones and hydrophobic zones characterized by at least one fatty chain.

The associative polymers that may be used according to the invention may be of anionic, cationic, amphoteric or, preferably, nonionic type.

Their weight concentration in the dye composition may range from about 0.01% to 10% of the total weight of the composition, and from about 0.0025% to 10% of the total weight of the composition. More preferably, this amount ranges from about 0.1% to 5% by weight in the dye composition and from about 0.025% to 10% in the ready-to-use composition.

Among the associative polymers of anionic type, mention may be made of polymers described below:

(I) polymers comprising at least one hydrophilic unit and at least one fatty-chain allyl ether unit, more particularly those whose hydrophilic unit consists of an ethylenic unsaturated anionic monomer, more particularly of a vinylcarboxylic acid and most particularly of an acrylic acid or a methacrylic acid or mixtures thereof. Anionic associative polymers of this type are described and prepared, according to an emulsion polymerization process, in patent EP-0 216 479.

Among these anionic associative polymers that are particularly preferred are crosslinked terpolymers of methacrylic acid, of ethyl acrylate and of polyethylene glycol (10 EO) stearyl alcohol ether (Steareth-10), in particular those sold by the company Allied Colloids under the names Salcare SC 80® and Salcare SC 90®, which are aqueous 30% emulsions of a crosslinked terpolymer of methacrylic acid, of ethyl acrylate and of steareth-10 allyl ether (40/50/10).

(II) polymers comprising at least one hydrophilic unit of unsaturated olefinic carboxylic acid type, and at least one hydrophobic unit of ($C_{10}$-$C_{30}$)alkyl ester of unsaturated carboxylic acid type.

Preferably, these polymers are chosen from those in which the hydrophilic unit of unsaturated olefinic carboxylic acid type corresponds to acrylic acid, methacrylic acid or ethacrylic acid units, and in which the hydrophobic unit is of ($C_{10}$-$C_{30}$)alkyl ester of unsaturated carboxylic acid type containing $C_{10}$-$C_{30}$ and preferably $C_{12}$-$C_{22}$ alkyl acrylate, methacrylate or ethacrylate units.

($C_{10}$-$C_{30}$) alkyl esters of unsaturated carboxylic acids according to the invention include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949.

Among the anionic associative polymers of this type that will be used more particularly are polymers formed from a monomer mixture essentially comprising acrylic acid, an alkyl acrylate ester containing from 12 to 22 carbon atoms, and a crosslinking agent, which is a well-known copolymerizable unsaturated polyethylenic monomer, for instance diallyl phthalate, allyl (meth)acrylate, divinylbenzene, (poly)ethylene glycol dimethacrylate and methylenebisacrylamide.

Among anionic associative polymers of this type that will be used more particularly are those consisting of from 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or alternatively those consisting of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Among the said above polymers, those most particularly preferred according to the present invention are the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

(III) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608® by the company Newphase Technologies.

(IV) acrylic terpolymers comprising about 20% to 70% by weight of a carboxylic acid containing α,β-monoethylenic unsaturation, about 20% to 80% by weight of a non-surfactant monomer containing α,β-monoethylenic unsaturation, about 0.5% to 60% by weight of a nonionic monourethane which is the product of reaction of a monohydric surfactant with a monoisocyanate containing monoethylenic unsaturation, such as those described in patent application EP-A-0 173 109 and more particularly the terpolymer described in Example 3, namely a methacrylic acid/methyl acrylate/behenyl dimethyl-meta-isopropenylbenzylisocyanate ethoxylated (40 EO) terpolymer, as an aqueous 25% dispersion.

(V) copolymers comprising among their monomers a carboxylic acid containing α,β-monoethylenic unsaturation and an ester of a carboxylic acid containing α,β-monoethylenic unsaturation and of an oxyalkylenated fatty alcohol.

Preferentially, these compounds also comprise as monomer an ester of a carboxylic acid containing α,β-monoethylenic unsaturation and of a $C_1$-$C_4$ alcohol.

An example of a compound of this type that may be mentioned is Aculyn 22® sold by the company Rohm & Haas, which is a methacrylic acid/ethyl acrylate/stearyl methacrylate oxyalkylenated terpolymer.

Among the associative polymers of cationic type that may be mentioned are:

(I) cationic associative polyurethanes, the family of which has been described by the Applicant in French patent application FR 2 811 993; it may be represented by the general formula (XVIII) below:

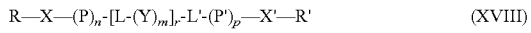

$$R\text{---}X\text{---}(P)_n\text{-}[L\text{-}(Y)_m]_r\text{-}L'\text{-}(P')_p\text{---}X'\text{---}R' \quad \text{(XVIII)}$$

in which:

R and R', which may be identical or different, represent a hydrophobic group or a hydrogen atom;

X and X', which may be identical or different, represent a group comprising an amine function optionally bearing a hydrophobic group, or alternatively the group L";

L, L' and L", which may be identical or different, represent a group derived from a diisocyanate;

P and P', which may be identical or different, represent a group comprising an amine function optionally bearing a hydrophobic group;

Y represents a hydrophilic group;

r is an integer between 1 and 100, preferably between 1 and 50 and in particular between 1 and 25;

n, m and p are each, independently of each other, between 0 and 1000;

the molecule containing at least one protonated or quaternized amine function and at least one hydrophobic group.

In one preferred embodiment of these polyurethanes, the only hydrophobic groups are the groups R and R' at the chain ends.

One preferred family of cationic associative polyurethanes is the one corresponding to formula (XVIII) described above and in which:

R and R' both independently represent a hydrophobic group,

X and X' each represent a group L", n and p are between 1 and 1000, and

L, L', L", P, P', Y and m have the meaning given above.

Another preferred family of cationic associative polyurethanes is the one corresponding to the formula above in which:

R and R' both independently represent a hydrophobic group, X and X' each represent a group L", n and p are 0, and L, L', L", Y and m have the meaning given above.

The fact that n and p are 0 means that these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e. compounds of the type RQ or R'Q, in which R and R' are as defined above and Q denotes a leaving group such as a halide, a sulfate, etc.

Yet another preferred family of cationic associative polyurethanes is the one corresponding to the formula above in which:

R and R' both independently represent a hydrophobic group,

X and X' both independently represent a group comprising a quaternary amine, n and p are zero, and L, L', Y and m have the meaning given above.

The number-average molecular mass of the cationic associative polyurethanes is preferably between 400 and 500 000, in particular between 1000 and 400 000 and ideally between 1000 and 300 000 g/mol.

The expression "hydrophobic group" means a radical or polymer containing a saturated or unsaturated, linear or branched hydrocarbon-based chain, which may contain one or more hetero atoms such as P, O, N or S, or a radical containing a perfluoro or silicone chain. When the hydrophobic group denotes a hydrocarbon-based radical, it comprises at least 10 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound.

By way of example, the hydrophobic group may be derived from a fatty alcohol such as stearyl alcohol, dodecyl alcohol or decyl alcohol. It may also denote a hydrocarbon-based polymer such as, for example, polybutadiene.

As regards the meaning of Y, the term "hydrophilic group" means a polymeric or non-polymeric water-soluble group.

By way of example, when it is not a polymer, mention may be made of ethylene glycol, diethylene glycol and propylene glycol.

When it is a hydrophilic polymer, in accordance with one preferred embodiment, mention may be made, for example, of polyethers, sulfonated polyesters, sulfonated polyamides or a mixture of these polymers. The hydrophilic compound is preferentially a polyether and in particular a poly(ethylene oxide) or poly(propylene oxide).

Although the presence of a hydrophilic group Y is optional, cationic associative polyurethanes comprising such a group are, however, preferred.

(II) quaternized cellulose derivatives and polyacrylates containing non-cyclic amine side groups.

The quaternized cellulose derivatives are, in particular:

quaternized celluloses modified with groups comprising at least one fatty chain, such as alkyl, arylalkyl or alkylaryl groups containing at least 8 carbon atoms, or mixtures thereof, quaternized hydroxyethylcelluloses modified with groups comprising at least one fatty chain, such as alkyl, arylalkyl or alkylaryl groups containing at least 8 carbon atoms, or mixtures thereof.

The alkyl radicals borne by the above quaternized celluloses or hydroxyethylcelluloses preferably contain from 8 to 30 carbon atoms. The aryl radicals preferably denote phenyl, benzyl, naphthyl or anthryl groups.

Examples of quaternized alkylhydroxyethyl-celluloses containing $C_8$-$C_{30}$ fatty chains that may be mentioned include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol, and the products Crodacel QM®, Crodacel QL® ($C_{1-2}$ alkyl) and Crodacel QS® ($C_{18}$ alkyl) sold by the company Croda.

Among the amphoteric associative polymers, mention may be made of those comprising at least one non-cyclic cationic unit. More particularly, the ones that are preferred are those prepared from or comprising 1 to 20 mol %, preferably 1.5 to 15 mol % and even more particularly 1.5 to 6 mol % of fatty-chain monomer relative to the total number of moles of monomers.

The amphoteric associative polymers that are preferred comprise or are prepared by copolymerizing:

1) at least one monomer (XIX) or (XX):

2) at least one monomer (XXI)

and 3) at least one monomer (XXII):

The monomers (XIX) and (XX) are, for example:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, dimethylaminopropylacrylamide, these monomers optionally being quaternized, for example with a $C_1$-$C_4$ alkyl halide or a $C_1$-$C_4$ dialkyl sulfate.

More particularly, the monomer (XIX) is chosen from acrylamidopropyltrimethylammonium chloride and methacrylamidopropyltrimethylammonium chloride.

The monomers (XXI) are for example acrylic acid, methacrylic acid, crotonic acid and 2-methylcrotonic acid. More particularly, the monomer (XXI) is acrylic acid.

The monomers (XXII) are preferably chosen from the group consisting of $C_{12}$-$C_{22}$ and more particularly $C_{16}$-$C_{18}$ alkyl acrylates or methacrylates.

The monomers constituting the fatty-chain amphoteric polymers of the invention are preferably already neutralized and/or quaternized.

The ratio of the number of cationic charges/anionic charges is preferably equal to about 1.

The amphoteric associative polymers according to the invention preferably comprise from 1 mol % to 10 mol % of the monomer comprising a fatty chain (monomer of formula (XIX), (XX) or (XXII)), and preferably from 1.5 mol % to 6 mol %.

The weight-average molecular weights of the amphoteric associative polymers according to the invention may range from 500 to 50 000 000 and are preferably between 10 000 and 5 000 000.

The amphoteric associative polymers according to the invention may also contain other monomers such as nonionic monomers and in particular such as $C_1$-$C_4$ alkyl acrylates or methacrylates.

Amphoteric associative polymers according to the invention are described and prepared, for example, in patent application WO 98/44012.

Among the amphoteric associative polymers according to the invention, the ones that are preferred are acrylic acid/ (meth)acrylamidopropyltrimethyl-ammonium chloride/ stearyl methacrylate terpolymers.

As associative polymers of nonionic type that may be used according to the invention, mention may be made of:

(1) celluloses modified with groups comprising at least one fatty chain; for example:

hydroxyethylcelluloses modified with groups comprising at least one fatty chain, such as alkyl, arylalkyl or alkylaryl groups, or mixtures thereof, and in which the alkyl groups are preferably $C_8$-$C_{22}$, for instance the product Natrosol Plus Grade 330 CS® ($C_{16}$ alkyls) sold by the company Aqualon, or the product Bermocoll EHM 100® sold by the company Berol Nobel, those modified with alkylphenyl polyalkylene glycol ether groups, such as the product Amercell Polymer HM-1500® (nonylphenyl polyethylene glycol (15) ether) sold by the company Amerchol.

(2) hydroxypropyl guars modified with groups comprising at least one fatty chain, such as the product Esaflor HM 22® ($C_{22}$ alkyl chain) sold by the company Lamberti, and the products RE210-18® ($C_{1-4}$ alkyl chain) and RE205-1® ($C_{20}$ alkyl chain) sold by the company Rhône-Poulenc.

(3) copolymers of vinylpyrrolidone and of fatty-chain hydrophobic monomers of which examples that may be mentioned include:

the products Antaron V216® or Ganex V216® (vinylpyrrolidone/hexadecene copolymer) sold by the company I.S.P.

the products Antaron V220® or Ganex V220® (vinylpyrrolidone/eicosene copolymer) sold by the company I.S.P.

(4) copolymers of $C_1$-$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®.

(5) copolymers of hydrophilic methacrylates or acrylates and of hydrophobic monomers comprising at least one fatty chain, such as, for example, the polyethylene glycol methacrylate/lauryl methacrylate copolymer.

(6) polyurethane polyethers comprising in their chain both hydrophilic blocks usually of polyoxyethylenated nature and hydrophobic blocks which may be aliphatic sequences alone and/or cycloaliphatic and/or aromatic sequences.

(7) polymers with an aminoplast ether skeleton containing at least one fatty chain, such as the Pure Thix® compounds sold by the company Sud-Chemie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In particular, it is possible for one or more pendent chains to be included. In addition, the polymer may comprise a hydrocarbon-based chain at one end or at both ends of a hydrophilic block.

The polyurethane polyethers may be multiblock, in particular in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, it is also possible to use Rheolate 205® containing a urea function, sold by the company Rheox, or Rheolate® 208, 204 or 212, and also Acrysol RM 184®.

Mention may also be made of the product Elfacos T210® containing a $C_{12-14}$ alkyl chain, and the product Elfacos T212® containing a $C_{18}$ alkyl chain, from Akzo.

The product DW 1206B® from Rohm & Haas containing a $C_{20}$ alkyl chain and a urethane linkage, sold at a solids content of 20% in water, may also be used.

It is also possible to use solutions or dispersions of these polymers, especially in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Rohm & Haas may also be used.

The polyurethane polyethers that may be used according to the invention are in particular those described in the article by G. Formum, J. Bakke and Fk. Hansen—Colloid Polym. Sci 271, 380.389 (1993).

It is even more particularly preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Rohm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl-isocyanate) (SMDI), at 35% by weight in a mixture of propylene glycol (39%) and water (26%)].

The compositions that are useful may also contain at least one surfactant.

The surfactants that are suitable for carrying out the present invention are especially the following:

(i) Anionic Surfactant(s):

By way of example of anionic surfactants that can be used, alone or as mixtures, in the context of the present invention, mention may be made in particular (non-limiting list) of salts (in particular alkali metal salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$-$C_{24}$)alkyl sulfosuccinates, ($C_6$-$C_{24}$)alkyl ether sulfosuccinates, ($C_6$-$C_{24}$) alkylamide sulfosuccinates; ($C_6$-$C_{24}$)alkyl sulfoacetates; ($C_6$-$C_{24}$)acyl sarcosinates; and ($C_6$-$C_{24}$)acyl glutamates. It is also possible to use ($C_6$-$C_{24}$)alkylpolyglycoside carboxylic esters such as alkylglucoside citrates, alkylpolyglycoside tartrates and alkylpolyglycoside sulfosuccinates, alkylsulfosuccinamates; acyl isethionates and N-acyl taurates, the alkyl or acyl radical of all of these different compounds preferably containing from 12 to 20 carbon atoms and the aryl radical preferably denoting a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; acyl lactylates in which the acyl radical contains 8 to 20 carbon atoms. It is also possible to use alkyl D-galactoside uronic acids and their salts, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and their salts, in particular those containing from 2 to 50 alkylene oxide groups, in particular ethylene oxide groups, and mixtures thereof.

(ii) Nonionic Surfactant(s):

The nonionic surfactants are, themselves also, compounds that are well known per se (see in particular in this respect "Handbook of Surfactants" by M. R. Porter, published by Blackie & Son (Glasgow and London), 1991, pp. 116-178) and their nature is not a critical factor in the context of the present invention. Thus, they can be chosen in particular from (non-limiting list) polyethoxylated or polypropoxylated, alkylphenols, alpha-diols or alcohols, having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, and amine oxides such as ($C_{10}$-$C_{14}$)alkylamine oxides or N-acylaminopropylmorpholine oxides.

(iii) Amphoteric or Zwitterionic Surfactant(s):

The amphoteric or zwitterionic surfactants, the nature of which is not a critical factor in the context of the present invention, can be, in particular (non-limiting list), aliphatic secondary or tertiary amine derivatives in which the aliphatic radical is a linear or branched chain containing 8 to 18 carbon atoms and containing at least one water-solubilizing anionic group (for example carboxylate, sulfonate, sulfate, phosphate or phosphonate); mention may also be made of ($C_8$-$C_{20}$) alkylbetaines, sulfobetaines, ($C_8$-$C_{20}$)alkylamido($C_1$-$C_6$) alkylbetaines or ($C_8$-$C_{20}$)alkylamido($C_1$-$C_6$)alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates.

These compounds are classified in the CTFA dictionary, 5th edition, 1993, under the names Disodium Cocoamphodiacetate, Disodium Lauroamphodiacetate, Disodium Caprylamphodiacetate, Disodium Caprylampho-diacetate, Disodium Cocoamphodipropionate, Disodium Lauroamphopropionate, Disodium Caprylamphodipropionate, Disodium Caprylamphodipropionate, Lauroamphodipropionic acid and Cocoamphodipropionic acid.

By way of example, mention may be made of the cocoamphodiacetate sold under the trade name Miranol C2M concentrate by the company Rhodia Chimie.

(iv) Cationic Surfactants:

Among the cationic surfactants, mention may be made in particular (non-limiting list) of: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The amounts of surfactants present in the composition according to the invention can range from 0.01% to 40% and preferably from 0.5% to 30% relative to the total weight of the composition.

The composition of the present invention may also comprise one or more oxidation dye precursors: one or more oxidation bases and/or one or more couplers. By way of example, the oxidation bases are chosen from para-phenylenediamines, bis(phenyl)alkylenediamines, para-aminophenols, ortho-aminophenols and heterocyclic bases and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloro-aniline, 2-p-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylene-diamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylene-diamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis (4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis (β-hydroxyethyl)-N,N'-bis(4-aminophenyl)tetramethylenediamine, N,N'-bis(4-methylaminophenyl)tetramethylene-diamine, N,N'-bis(ethyl)-N,N'-bis(4'-amino-3'-methyl-phenyl) ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026

978 and GB 1 153 196, for instance 2,5-diaminopyridine, 2-(4-methoxyphenyl)amino-3-aminopyridine, and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamino, (3-aminopyrazolo[1,5-a]pyrid-7-yl)methanol, 2-(3-amino-pyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]-pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxy-ethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triamino-pyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof.

The additional oxidation base(s) present in the composition of the invention is (are) generally present in an amount ranging from 0.001% to 20% by weight approximately, and preferably ranging from 0.005% to 6%, relative to the total weight of the dye composition.

The composition according to the invention preferably contains one or more couplers conventionally used for dyeing keratin fibres Among these couplers, mention may be made especially of meta-phenylenediamines, meta-diphenols, naphthalene-based couplers and heterocyclic couplers, and the addition salts thereof.

Examples that may be mentioned include 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethyl-amino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)-amino-3,4-methylenedioxybenzene and 2,6-bis(β-hydroxy-ethylamino)toluene, and the addition salts thereof.

The coupler(s) is (are) generally present in an amount ranging from 0.001% to 20% and preferably ranging from 0.005% to 6% by weight approximately relative to the total weight of the dye composition.

In general, the addition salts of the oxidation bases and couplers that may be used in the context of the invention are chosen especially from the addition salts with an acid, such as the hydrochlorides, hydrobromides, sulfates, citrates, succinates, tartrates, lactates, tosylates, benzenesulfonates, phosphates and acetates, and the addition salts with a base, such as sodium hydroxide, potassium hydroxide, ammonia, amines or alkanolamines.

The compositions that are useful may also contain one or more additional direct dyes, which may especially be chosen from neutral, acidic or cationic nitrobenzene direct dyes, neutral, acidic or cationic azo direct dyes, neutral, acidic or cationic quinone and in particular anthraquinone direct dyes, azine direct dyes, triarylmethane direct dyes, indoamine direct dyes and natural direct dyes.

Among the benzenic direct dyes, mention may be made, in a non-limiting manner, of the following compounds:
1,4-diamino-2-nitrobenzene,
1-amino-2-nitro-4-(β-hydroxyethylamino)benzene,
1-amino-2-nitro-4-bis(β-hydroxyethyl)aminobenzene,
1,4-bis(β-hydroxyethylamino)-2-nitrobenzene,
1-β-hydroxyethylamino-2-nitro-4-bis(β-hydroxyethyl-amino)benzene,
1-β-hydroxyethylamino-2-nitro-4-aminobenzene,
1-β-hydroxyethylamino-2-nitro-4-(ethyl)(β-hydroxy-ethyl) aminobenzene,
1-amino-3-methyl-4-β-hydroxyethylamino-6-nitrobenzene,
1-amino-2-nitro-4-β-hydroxyethylamino-5-chloro-benzene,
1,2-diamino-4-nitrobenzene,
1-amino-2-β-hydroxyethylamino-5-nitrobenzene,
1,2-bis(β-hydroxyethylamino)-4-nitrobenzene,
1-amino-2-[tris(hydroxymethyl)methylamino]-5-nitrobenzene,
1-hydroxy-2-amino-5-nitrobenzene,
1-hydroxy-2-amino-4-nitrobenzene,
1-hydroxy-3-nitro-4-aminobenzene,
1-hydroxy-2-amino-4,6-dinitrobenzene,
1-β-hydroxyethyloxy-2-β-hydroxyethylamino-5-nitro-benzene,
1-methoxy-2-β-hydroxyethylamino-5-nitrobenzene,
1-β-hydroxyethyloxy-3-methylamino-4-nitrobenzene,
1-β,γ-dihydroxypropyloxy-3-methylamino-4-nitrobenzene,
1-β-hydroxyethylamino-4-β,γ-dihydroxypropyloxy-2-nitrobenzene,
1-β,γ-dihydroxypropylamino-4-trifluoromethyl-2-nitrobenzene,
1-β-hydroxyethylamino-4-trifluoromethyl-2-nitro-benzene,
1-β-hydroxyethylamino-3-methyl-2-nitrobenzene,
1-β-aminoethylamino-5-methoxy-2-nitrobenzene, 1-hydroxy-2-chloro-6-ethylamino-4-nitrobenzene,
1-hydroxy-2-chloro-6-amino-4-nitrobenzene,
1-hydroxy-6-[bis(β-hydroxyethyl)amino]-3-nitro-benzene,
1-β-hydroxyethylamino-2-nitrobenzene,
1-hydroxy-4-β-hydroxyethylamino-3-nitrobenzene.

Among the azo direct dyes that may be used according to the invention, mention may be made of the cationic azo dyes described in patent applications WO 95/15144, WO 95/01772 and EP 714 954, the content of which forms an integral part of the invention.

Among these compounds, mention may be made most particularly of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulfate.

Among the azo direct dyes that may also be mentioned are the following dyes described in the Colour Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-amino-diphenylazo)-2-methyl-4-[bis(β-hydroxyethyl)amino]-benzene and 4-hydroxy-3-(2-methoxyphenylazo)-1-naphthalenesulfonic acid.

Among the quinone direct dyes that may be mentioned are the following dyes:

Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds:
1-N-methylmorpholiniumpropylamino-4-hydroxyanthraquinone,
1-aminopropylamino-4-methylaminoanthraquinone,
1-aminopropylaminoanthraquinone,
5-β-hydroxyethyl-1,4-diaminoanthraquinone,
2-aminoethylaminoanthraquinone,
1,4-bis(β,γ-dihydroxypropylamino)anthraquinone.

Among the azine dyes that may be mentioned are the following compounds: Basic Blue 17, Basic Red 2.

Among the triarylmethane dyes that may be used according to the invention, mention may be made of the following compounds:

Basic Green 1, Acid Blue 9, Basic Violet 3, Basic Violet 14, Basic Blue 7, Acid Violet 49, Basic Blue 26, Acid Blue 7.

Among the indoamine dyes that may be used according to the invention, mention may be made of the following compounds:
2-β-hydroxyethylamino-5-[bis(β-4'-hydroxyethyl)-amino]anilino-1,4-benzoquinone;
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinoneimine;
3-N(3'-chloro-4'-methylamino)phenylureido-6-methyl-1,4-benzoquinoneimine;
3-[4'-N-(ethylcarbamylmethyl)amino]phenylureido-6-methyl-1,4-benzoquinoneimine.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes may also be used, and especially henna-based poultices or extracts.

The direct dye(s) preferably represent(s) from 0.001% to 20% by weight approximately, and even more preferably from 0.005% to 10% by weight approximately, relative to the total weight of the aqueous solution in which they are present.

The pH of the compositions that are useful is generally between 2 and 12 approximately and preferably between 3 and 8. It may be adjusted to the desired value by means of acidifying or basifying agents usually used for dyeing keratin fibres, or alternatively using standard buffer systems.

Among the acidifying agents that may be mentioned, for example, are mineral or organic acids such as hydrochloric acid, orthophosphoric acid, sulfuric acid, carboxylic acids, for instance acetic acid, tartaric acid, citric acid or lactic acid, and sulfonic acids.

Among the basifying agents that may be mentioned, for example, are aqueous ammonia, alkaline carbonates, alkanolamines such as monoethanolamine, diethanolamine and triethanolamine and derivatives thereof, sodium hydroxide, potassium hydroxide and the compounds of formula (II) below:

$$\begin{array}{c} R_a \quad\quad R_b \\ \diagdown\quad\quad\diagup \\ N\text{-}W\text{-}N \\ \diagup\quad\quad\diagdown \\ R_c \quad\quad R_d \end{array} \quad (II)$$

in which W is a propylene residue optionally substituted with a hydroxyl group or a $C_1$-$C_4$ alkyl radical; $R_a$, $R_b$, $R_c$, and $R_d$, which may be identical or different, represent a hydrogen atom or a $C_1$-$C_4$ alkyl or $C_1$-$C_4$ hydroxyalkyl radical.

When the composition comprises at least one oxidation dye precursor or when it is desired to perform lightening dyeing, an oxidizing agent may be used.

The oxidizing agents conventionally used for the oxidation dyeing of keratin fibres are, for example, hydrogen peroxide, urea peroxide, alkali metal bromates, persalts such as perborates and persulfates, peracids and oxidase enzymes, among which mention may be made of peroxidases, two-electron oxidoreductases such as uricases, and four-electron oxygenases, for instance laccases. Hydrogen peroxide is particularly preferred.

This oxidizing agent may also be present in either of the compositions that are useful in the invention or applied independently.

The oxidizing composition may also contain various adjuvants conventionally used in hair dye compositions and as defined above.

According to the process of the invention, the leave-in time for each of the compositions is not limiting. It may range from a few seconds to one hour. According to one particular embodiment, the duration of the pretreatment using the aqueous solution containing the cationic polymer is about one minute and the duration of the dyeing step using the anionic coloured polymer is less than five minutes.

The rinsing steps are performed in a conventional manner, generally using water.

The process of the invention is performed at a temperature ranging between room temperature and 200° C. and preferably between room temperature and 60° C.

A subject of the invention is also a kit for dyeing keratin fibres, comprising a first compartment containing a composition containing one or more cationic polymers as defined above, and a second compartment comprising a composition containing one or more anionic coloured polymers as defined above. According to one particular embodiment, at least the first compartment contains one or more organic and/or mineral salts.

The examples that follow serve to illustrate the invention without, however, being limiting in nature.

EXAMPLES

Example 1

A solution containing 3%, by mass of active material, of the polymer of formula (8) sold under the name Mexomer PO by Chimex in water is applied to a bleached lock. After a leave-in time of three minutes, the lock is rinsed. An aqueous 0.5 g % solution of poly S-119 is then applied. After a leave-in time of one minute, the lock is rinsed.

The lock thus treated has a strong coppery colour, which is uniform along the fibre.

Under the effect of water, the lock thus dyed does not bleed or lose its colour.

Moreover, when this lock is washed using a shampoo, it totally loses its coppery colour.

Example 2

A solution containing 3%, by mass of active material, of the polymer of formula (W) sold under the name Mexomer PO by Chimex in water containing one mole per litre of NaCl is applied to a lock of dark chestnut-brown hair. After a leave-in time of three minutes, the lock is rinsed with water. An aqueous solution containing 0.5 mol per litre of NaCl and 0.5 g % of Poly S-119 is then applied to this lock. After a leave-in time of one minute, the lock is rinsed.

A very visible green tint is then observed on the lock. The colour is fixed uniformly and aesthetically along the fibre.

The calorimetric measurements for the lock (Minolta CM-2002 spectrocolorimeter) indicate two maximum absorbance wavelengths: 410 nm and 610 nm (components of the observed green), whereas in solution or on fair hair, the maximum absorbance length is 430 nm (orange).

Under the effect of water, the lock thus dyed does not bleed or lose its colour.

Moreover, when this lock is washed using a shampoo, it totally loses its green colour.

The invention claimed is:

1. A process for dyeing keratin fibers comprising:
    applying to the fibers a cosmetic composition comprising at least one cationic polymer;
    rinsing the keratin fibers;
    applying to the fibers a cosmetic composition comprising at least one anionic colored polymer is chosen from:

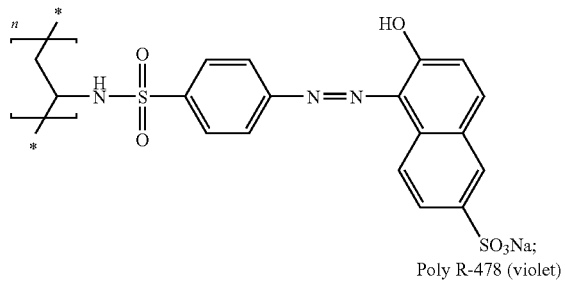

Poly S-119 (orange)

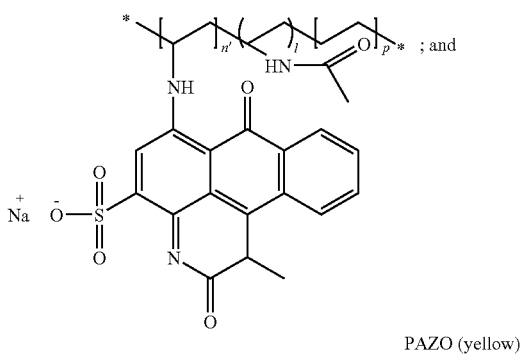

Poly R-478 (violet)

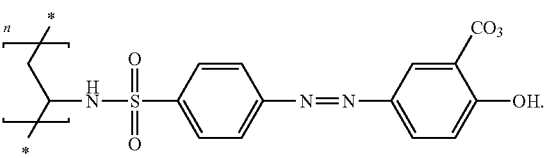

PAZO (yellow)

wherein
    n is an integer ranging from 1 to 500; and
    the sum of n', l, and p is 1; and
    rinsing the keratin fibers, thereby providing temporary coloration to said keratin fibers.

2. A process according to claim 1, wherein the at least one cationic polymer is polylysine.

3. A process according to claim 1, wherein the at least one cationic polymer is chosen from polymers comprising a quaternary ammonium group.

4. A process according to claim 1, wherein the at least one cationic polymer has the formula W:

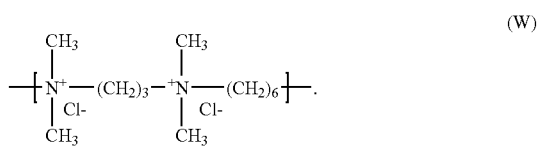

5. A process according to claim 1, wherein the at least one cationic polymer is present in an aqueous composition in an amount ranging from 0.01% to 20% by weight, relative to the total weight of the composition.

6. A process according to claim 1, wherein the at least one anionic colored polymer is present in an aqueous composition in an amount ranging from 0.01% to 20%.

7. A process according to claim 1, wherein the at least one anionic colored polymer is present in an aqueous composition in an amount ranging from 0.1% to 5%.

8. A process according to claim 1, wherein the cosmetic composition comprising the at least one cationic polymer and/or the cosmetic composition comprising the at least one anionic colored polymer further comprises at least one salt chosen from organic salts and mineral salts.

9. A process according to claim 8, wherein the at least one salt is chosen from sodium citrate, sodium chloride, ammonium sulfate, magnesium chloride and calcium chloride.

10. A process according to claim 8, wherein the at least one salt is present in an amount ranging from $10^{-4}$ to 2 mol/l.

11. A process according to claim 8, wherein the at least one salt is present in an amount ranging from $10^{-2}$ to 1 mol/l.

12. A process according to claim 1, wherein the keratin fibers are dark hair.

13. A process according to claim 1, wherein the cosmetic composition comprising the at least one cationic polymer and/or the cosmetic composition comprising the at least one anionic colored polymer further comprises at least one additive chosen from anionic, cationic, nonionic, amphoteric surfactants, zwitterionic surfactants; anionic polymers, cationic polymers, nonionic polymers, amphoteric polymers zwitterionic polymers; mineral thickeners, organic thickeners; antioxidants; penetrants; sequestrants; fragrances; buffers; dispersants; conditioning agents; film-forming agents; ceramides; preserving agents; opacifiers; and solvents.

14. A process according to claim 13, wherein the additives present in the cosmetic composition comprising the at least one cationic polymer and/or the cosmetic composition comprising the at least one anionic colored polymer do not bear charges opposite to the charge of the polymer.

15. A kit for temporarily dyeing keratin fibers comprising a first compartment comprising a cosmetic composition wherein the cosmetic composition in said first compartment comprises at least one cationic polymer having the formula W:

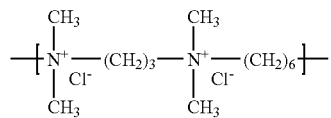

(W)

wherein said cationic polymer is present in an aqueous composition in an amount ranging from 0.01% to 20% by weight, relative to the total weight of the composition; and a second compartment comprising a cosmetic composition wherein the cosmetic composition in said second compartment comprises at least one anionic colored polymer, wherein said anionic polymer comprises an anionic chromophore substituted with at least one group chosen from sulfonate, carboxylate, phosphate, phosphonate and sulfate, and is present in an aqueous composition in an amount ranging from 0.01% to 20% by weight, relative to the total weight of the composition wherein the at least one anionic colored polymer is chosen from:

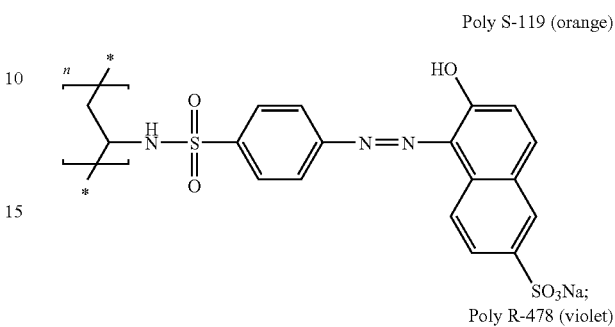

Poly S-119 (orange)

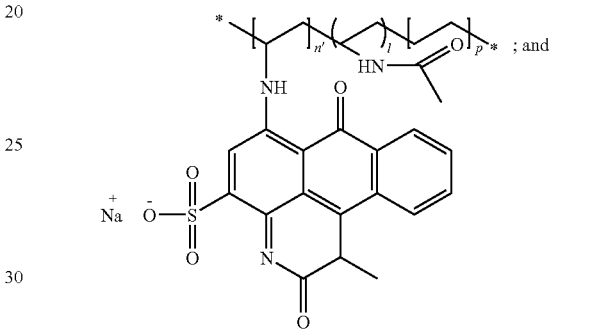

Poly R-478 (violet)

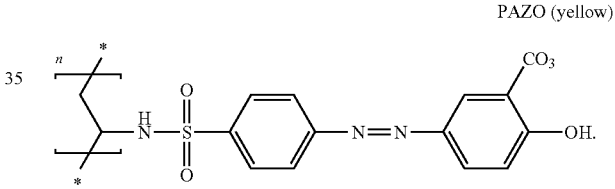

PAZO (yellow)

wherein
n is an integer ranging from 1 to 500; and
the sum of n', l, and p is 1.

16. A kit according to claim 15, wherein the first compartment contains at least one salt chosen from organic salt and mineral salt.

17. A kit according to claims 15, wherein the at least one cationic polymer and the at least one anionic colored polymer are aqueous.

* * * * *